(12) United States Patent
Rajagopalan

(10) Patent No.: US 7,294,738 B2
(45) Date of Patent: Nov. 13, 2007

(54) PHOSPHOROUS CONTAINING STEROID MIMICS

(76) Inventor: Raghavan Rajagopalan, 5097 Neptune Dr., Solon, OH (US) 44139

( * ) Notice: Subject to any disclaimer, the term of this patent is extended or adjusted under 35 U.S.C. 154(b) by 0 days.

(21) Appl. No.: 10/992,906

(22) Filed: Nov. 19, 2004

(65) Prior Publication Data

US 2005/0137170 A1    Jun. 23, 2005

Related U.S. Application Data

(60) Provisional application No. 60/523,358, filed on Nov. 19, 2003.

(51) Int. Cl.
*C07F 9/6512* (2006.01)
*C07D 471/12* (2006.01)

(52) U.S. Cl. .................... 562/19; 544/1; 544/244; 544/247; 424/1.37; 424/9.2

(58) Field of Classification Search ............ 424/1.37, 424/9.2, 1.77; 544/1, 244, 247; 562/19
See application file for complete search history.

(56) References Cited

U.S. PATENT DOCUMENTS 5,602,236 A * 2/1997 Rajagopalan ............... 534/10

OTHER PUBLICATIONS

Symmes et al. A new synthesis of phosphasteroids employing the McCormack cycloaddition for construction of the D-ring. Tetrahedron Letters 1977, pp. 335-338.
Bodalski et al. An efficient synthesis of the entaniomeric 17-phosphasteroid system. J. Org. Chem. 1982, vol. 47, pp. 2219-2220.
Chi et al. Selective formation of heterodimeric bis-bidentate aminothiol-oxometal complexes of rhenium (V). J. Am. Chem. Soc. 1993, vol. 115, pp. 7045-7046.
Chi et al. Homodimeric and heterodimeric bis(amino thiol) oxometal complexes with rhenium (V) and technetium (V). J. Med. Chem. 1994, vol. 37, pp. 928-937.
Hom et al. Synthesis of tetradentate oxorhenium (V) complex mimic of a steroidal estrogen. J. Org. Chem. 1997, vol. 62, pp. 6290-6297.

* cited by examiner

*Primary Examiner*—Charanjit S. Aulakh

(57) ABSTRACT

The present invention discloses novel steroid mimics wherein a tri- or tetravalent phosphorous atom is isosterically substituted at any one of the seventeen positions occupied by the carbon atom in the steroidal skeleton, and wherein each adjacent position to the phosphorous is either unsubstituted or optionally substituted by nitrogen or an oxygen atom to satisfy the valency of said phosphorous atom. The invention is illustrated schematically below using both aromatic and non-aromatic steroids. Although the isosteric substitution

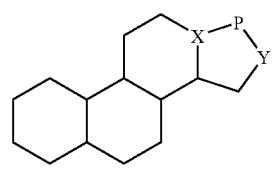

3

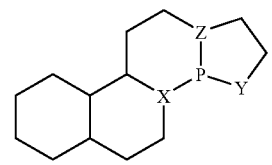

4

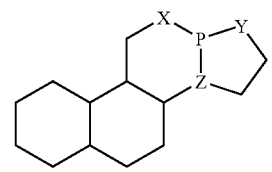

5

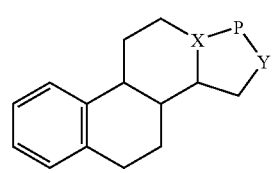

6

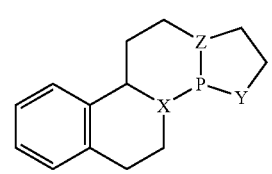

7

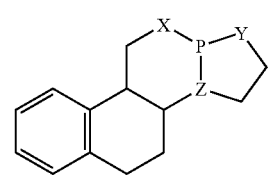

8 phosphorous atom in the above structures 3–7 is indicated at 13, 14, and 17 positions, it is to be noted that the phosphorous can be substituted at any one of the seventeen positions in non-aromatic or eleven positions in aromatic steroids. The phosphorous atom may be trivalent or tetravalent, and may be radioactive or non-radioactive. The adjacent atoms, X, Y, or Z may be carbon, oxygen, or nitrogen. Other positions in the steroid mimics 3–8 may be optionally substituted alkyl, aryl, or other polar or non-polar functional groups to optimize biodistribution, receptor binding, and pharmacokinetic properties.

4 Claims, No Drawings

PHOSPHOROUS CONTAINING STEROID MIMICS

FIELD OF THE INVENTION

This invention relates to heteroatom-containing compositions which mimic the molecular framework of a steroid. In particular, the present invention discloses novel phosphasteroids wherein the phosphorous atom is isosterically substituted at the positions previously occupied by a carbon atom in the steroidal skeleton.

BACKGROUND OF THE INVENTION

It is to be noted that throughout this application various publications are referenced by Arabic numerals within brackets. Full citations for these publications are listed at the end of the specification. The disclosures of these publications are hereby incorporated by reference in their entireties into this application in order to more fully describe the state of the art to which this invention pertains.

Targeted delivery of medically useful elements to a particular site continues to be of considerable importance in diagnosis, prognosis, and therapy of various lesions [1]. For example, gadolinium is used extensively for magnetic resonance imaging (MRI); barium and iodine are used for X-ray computed tomography (CT); technetium, indium, lutetium, samarium, and iodine are used for planar imaging and single photon emission tomography (SPECT); gallium and fluorine are used for positron emission tomography (PET); rhenium, samarium, yttrium, lutetium, and phosphorous are used for radiotherapy; and europium, ruthenium, and rhenium have potential utility for optical imaging and optical tomography. In particular, $^{32}$P, a β-emitting radioisotope of phosphorous, has considerable radiotherapeutic potential for various lesions depending on its incorporation into a selected molecular carrier. For example, incorporation of $^{32}$P into a steroid receptor binding molecules such as androgens, estrogens, antiestrogens, progestins, and the like may be useful for the treatment of steroid receptor positive tumors; incorporation into somatostatin receptor binding molecules such as octreotide may be useful for the treatment of neuroendocrine tumors; or incorporation into carbohydrate receptor binding molecules such as selectins or integrins may be useful for inflammatory process.

Conventional bioconjugate method of delivering diagnostic and therapeutic agents, both small molecules and macromolecules, such as drugs, enzymes, metal complexes, fluorescent and radioactive probes, and the like to a particular tissue involves the external attachment of these agents to a targeting carrier whose size is typically considerably larger than the effector molecules. This methodology has been referred to as "external bifunctional" approach, and has been quite successful in the development of in vitro diagnostic products. However, one of most vexing problems in bioconjugate chemistry with respect to the development of in vivo diagnostic and therapeutic agents is that the external attachment of a radionuclide complex to small molecule carriers almost always impedes receptor binding [2]. This problem can be readily resolved by the use of macromolecular carriers such as antibodies or reasonably large peptides where the epitope topology is not much altered. An epitope is a specific region of the molecule that is actually involved in the adhesion of the effector and carrier through the intermolecular forces. Unfortunately, macromolecular bioconjugates present many problems with respect to bioavailability, pharmacokinetics, and biodistribution. Moreover, for nuclear medicine applications, the external bifunctional agents presents additional radiotoxicity of critical non-target tissues such as the liver and the kidney due to unacceptably large percent injected dose to and poor clearance from these organs. In order to address both of the aforementioned problems, viz., receptor binding and bioavailability, we have previously introduced a general concept referred to as 'internal bifunctional' approach or 'small molecule drug mimics' wherein the medically useful atom is integrated into a known effector molecule thereby preserving the overall size and shape of the original molecule. This approach was based on the well established principle that antibodies, enzymes, and receptors are multispecific, i.e., they will bind to molecules that are topologically similar to the natural antigens, substrates, or ligands. The concept of radionuclide metal ion based drug mimics was independently proposed by Rajagopalan [3, 4] and Katzenellenbogen [5]. Katzenellenbogen's work on steroid mimics confirmed experimentally that the idea of integrating a metal ion into natural receptor ligands is a viable strategy for targeted delivery of diagnostically and therapeutically useful radionuclides to target tissues [2, 5–7].

Our previous work on steroid mimics focused on isosteric substitution of metal ions such as technetium and rhenium into various positions in aromatic and non-aromatic steroidal framework as illustrated schematically by generic structures 1 and 2 [4]. A considerable difficulty with respect to incorporating a metal ion into a carbon framework is the deviation

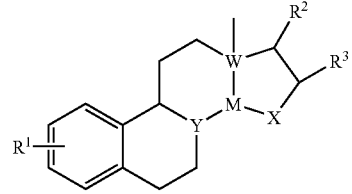

1: Aromatic Steroid Mimic

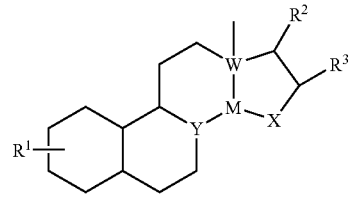

2: Non-Aromatic Steroid Mimic from tetrahedral geometry. For example, Tc(V) and Re(V) oxidation state forms a square pyramidal geometry, which may contribute to reduced receptor binding capability. Furthermore, $^{186}$Re obtained from the generator is not carrier free, i.e., only 5% is in the radioactive form; the rest of the material is the non-radioactive ('cold') isotope of rhenium. Therefore, this presents a formidable challenge to prepare steroid mimics with very high specific activity needed for radiotherapeutic purposes. In contrast, $^{32}$P can be obtained in a carrier-free from. Thus, there is a need in the art to prepare novel radiodiagnostic and radiotherapeutic steroidal compositions with high specific activity and having high affinity for steroid receptors. Accordingly, the present invention focuses phosphorous-based steroid mimics. Although phosphasteroids have been known for sometime [8, 9], surprisingly there has not been much activity in developing them into medically useful products. Introducing a phosphorous atom into the steroidal skeleton solves two key problems: (a)

the preservation of tetrahedral geometry, and (b) the preparation of steroid mimics having very high specific activity. In addition, steroids are transported across cell membrane from the blood to the cytoplasm via steroid binding proteins (SBP) [10]. Since the phosphorous containing steroid mimics of the present invention have same topology at the original steroids, it is anticipated that the mimics will bind to SBP and transported into the cell in the same manner as the native steroid molecules.

SUMMARY OF THE INVENTION

The present invention discloses novel steroid mimics wherein a tri- or tetravalent phosphorous atom is isosterically substituted at any one of the seventeen positions occupied by the carbon atom in the steroidal skeleton, and wherein each adjacent position to the phosphorous is either unsubstituted or optionally substituted by nitrogen or an oxygen atom to satisfy the valency of said phosphorous atom. The number of adjacent substitutions depends on whether a secondary, tertiary, or quaternary position is substituted; substitution at the secondary center requires two substitutions, and tertiary and quaternary centers require three substitutions. The invention is illustrated schematically below using both aromatic and

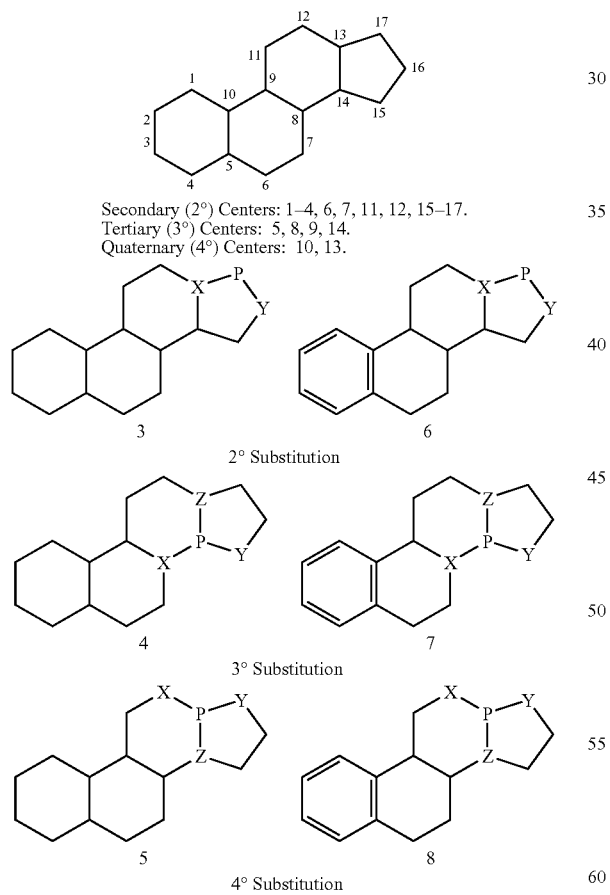

non-aromatic steroids. Although the isosteric substitution of phosphorous atom in the above structures is indicated at 13, 14, and 17 positions, it is to be noted that the phosphorous can be substituted at any one of the seventeen positions in non-aromatic or eleven positions in aromatic steroids. The phosphorous atom may be trivalent or tetravalent, and may be radioactive or non-radioactive. The adjacent atoms, X, Y, or Z may be carbon, oxygen, or nitrogen. Other positions in the steroid mimics 3–8 may be optionally substituted alkyl, aryl, or other polar or non-polar functional groups to optimize biodistribution, receptor binding, and pharmacokinetic properties. In particular, 7α, 11β, and 17α positions in steroids have been shown to tolerate bulky substituents, including metal complexes [11–13], and the substitutions at these positions in the steroid mimics of this invention are also contemplated.

DETAILED DESCRIPTION OF THE INVENTION

The present invention discloses novel aromatic phosphorous steroid mimic compositions of Formulas 9–12, wherein P is —P— or —P═O. X and Y are independently —O— or —NR$^4$. R$^1$ to R$^3$ are independently selected from the group consisting of hydrogen; $C_1$–$C_{10}$ alkyl; hydroxyl; carboxyl; $C_1$–$C_{10}$ acyl; $C_1$–$C_{10}$ hydroxyalkyl; $C_1$–$C_{10}$ alkoxycarbonyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkxoycarbonyl. R$^4$ is selected from the group consisting of hydrogen; $C_1$–$C_{10}$ alkyl; $C_1$–$C_{10}$ hydroxyalkyl; $C_1$–$C_{10}$ alkoxycarbonylalkyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino $C_1$–$C_{10}$ alkylamino, $C_1$–$C_{10}$ dialkylamino, and $C_1$–$C_{10}$ alkoxycarbonyl.

A preferred embodiment of the present invention is represented by Formula 9,

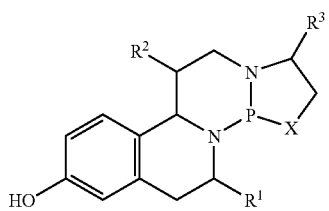

Formula 9 wherein P is —P— or —P=O. X is —O— or —NR$^4$. $R^1$ to $R^3$ are independently selected from the group consisting of hydrogen; $C_1$–$C_{10}$ alkyl; carboxyl; $C_1$–$C_{10}$ hydroxyalkyl; $C_1$–$C_{10}$ alkoxycarbonyl; $C_5$–$C_{10}$ aryl unsubstituted or substituted with $C_1$–$C_{10}$ alkyl, hydroxyl, $C_1$–$C_{10}$ alkoxyl, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl. $R^4$ is selected from the group consisting of hydrogen; $C_1$–$C_{10}$ alkyl; $C_1$–$C_{10}$ hydroxyalkyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl.

Another preferred embodiment of the present invention is represented by Formula 10,

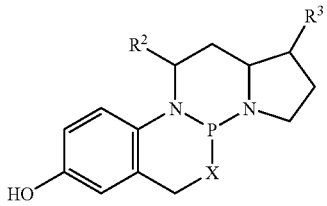

Formula 10 wherein P is —P— or —P=O. X is —O— or —NR$^4$. $R^2$ and $R^3$ are independently selected from the group consisting of hydrogen; $C_1$–$C_{10}$ alkyl; hydroxyl; carboxyl; $C_1$–$C_{10}$ acyl; $C_1$–$C_{10}$ hydroxyalkyl; $C_1$–$C_{10}$ alkoxycarbonyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl. $R^4$ is selected from the group consisting of hydrogen; $C_1$–$C_{10}$ alkyl; $C_1$–$C_{10}$ hydroxyalkyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl.

Another preferred embodiment of the present invention is represented by Formula 11,

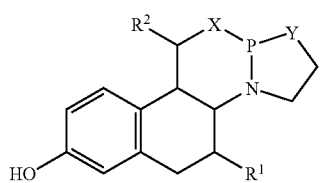

Formula 11 wherein P is —P— or —P=O. X and Y are independently —O— or —NR$^4$. $R^1$ and $R^2$ are independently selected from the group consisting of hydrogen; $C_1$–$C_{10}$ alkyl; carboxyl; $C_1$–$C_{10}$ hydroxyalkyl; $C_1$–$C_{10}$ alkoxycarbonyl; $C_5$–$C_{10}$ aryl unsubstituted or substituted with $C_1$–$C_{10}$ alkyl, hydroxyl, $C_1$–$C_{10}$ alkoxyl, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl. $R^4$ is selected from the group consisting of hydrogen; $C_1$–$C_{10}$ alkyl; $C_1$–$C_{10}$ hydroxyalkyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, and $C_1$–$C_{10}$ alkxoylcarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl.

Another preferred embodiment of the present invention is represented by Formula 12,

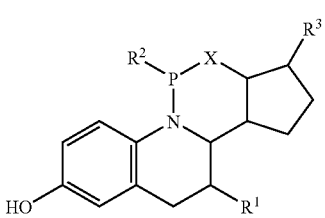

Formula 12 wherein P is —P— or —P=O. X is —O— or —NR$^4$. R$^1$ to R$^3$ are independently selected from the group consisting of hydrogen; C$_1$–C$_{10}$ alkyl; carboxyl; C$_1$–C$_{10}$ hydroxyalkyl; C$_1$–C$_{10}$ alkoxycarbonyl; C$_5$–C$_{10}$ aryl unsubstituted or substituted with C$_1$–C$_{10}$ alkyl, hydroxyl, C$_1$–C$_{10}$ alkoxyl, trihaloalkyl, carboxyl, C$_1$–C$_{10}$ acyl, C$_1$–C$_{10}$ hydroxyalkyl, amino, C$_1$–C$_{10}$ alkylamino, C$_1$–C$_{10}$ dialkylamino, and C$_1$–C$_{10}$ alkoxycarbonyl; and C$_5$–C$_{10}$ arylalkyl unsubstituted or substituted with C$_1$–C$_{10}$ alkyl, hydroxyl, C$_1$–C$_{10}$ alkoxyl, cyano, halo, trihaloalkyl, carboxyl, C$_1$–C$_{10}$ acyl, C$_1$–C$_{10}$ hydroxyalkyl, amino, C$_1$–C$_{10}$ alkylamino, C$_1$–C$_{10}$ dialkylamino, and C$_1$–C$_{10}$ alkoxycarbonyl. R$^4$ is selected from the group consisting of hydrogen; C$_1$–C$_{10}$ alkyl; C$_1$–C$_{10}$ hydroxyalkyl; C$_5$–C$_{10}$ aryl unsubstituted or substituted with C$_1$–C$_{10}$ alkyl, hydroxyl, C$_1$–C$_{10}$ alkoxyl, cyano, halo, trihaloalkyl, carboxyl, C$_1$–C$_{10}$ acyl, C$_1$–C$_{10}$ hydroxyalkyl, amino, C$_1$–C$_{10}$ alkylamino, C$_1$–C$_{10}$ dialkylamino, and C$_1$–C$_{10}$ alkoxycarbonyl; and C$_5$–C$_{10}$ arylalkyl unsubstituted or substituted with C$_1$–C$_{10}$ alkyl, hydroxyl, C$_1$–C$_{10}$ alkoxyl, cyano, halo, trihaloalkyl, carboxyl, C$_1$–C$_{10}$ acyl, C$_1$–C$_{10}$ hydroxyalkyl, amino, C$_1$–C$_{10}$ alkylamino, C$_1$–C$_{10}$ dialkylamino, and C$_1$–C$_{10}$ alkoxycarbonyl.

The compounds of the present invention can be prepared by the methods well known in the art. Compounds belonging to Formula 9 can be prepared by the according to the method

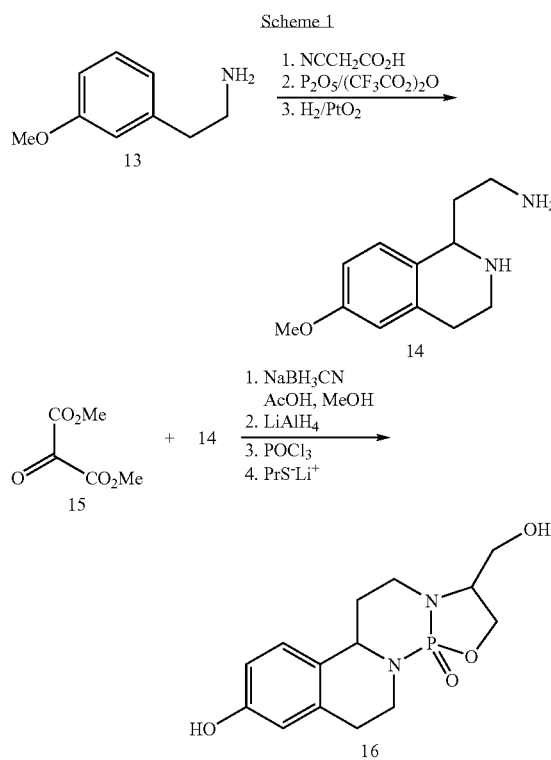

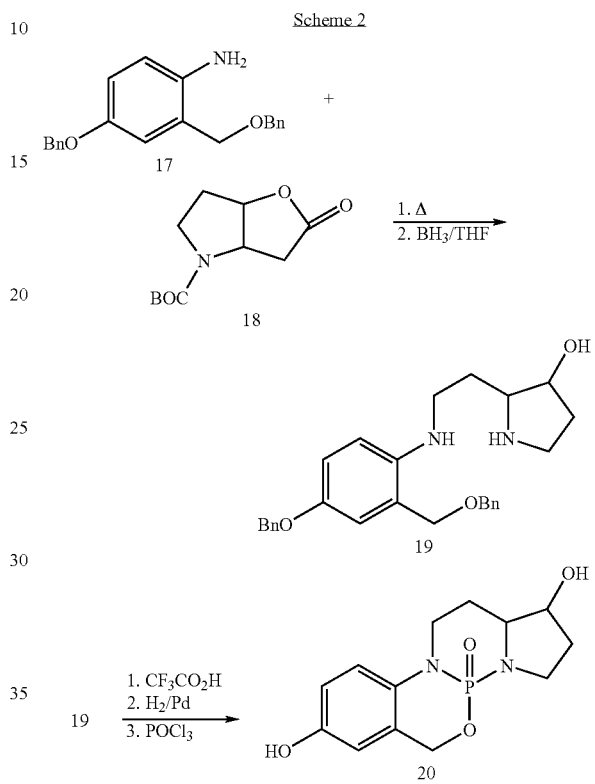

similar to the one for the specific steroid mimic 16 outlined in Scheme 1. The key step in this process is the construction of the tetrahydroisoquinoline intermediate 11, which can be either accomplished by Bischer-Napieralski cyclization followed by reduction, or by one-step Pictet-Spengler cyclization. Substitutions at the 7, 11, and 17 positions can be introduced by selecting appropriate starting materials. For example, 7 substituted derivatives can be prepared 3-methoxyphenylalaine; 11 substituted derivatives can be prepared from α-cyanoacetate derivatives; and 17 substituted derivatives can be prepared by elaborating the 17-hydroxymethyl group in 16.

Compounds belonging to Formula 10 can be prepared according to the method similar to the one for the specific steroid mimic 20 outlined in Scheme 2. The amine 13 can be prepared by standard methods from 5-hydroxy-2-nitrobenzoic acid. The unprotected derivative of lactone 18, the 'Geissman-Waiss lactone, has used extensively as a key intermediate for the synthesis of pyrrolizidine alkaloids. The original synthesis of this lactone is reported by Geissman and Waiss [14], which is incorporated herein by reference in its entirety.

Compounds belonging to Formula 11 can be prepared by the according to the method similar to the one for the specific steroid mimics 23 and 24 outlined in Scheme 3. The ester 21 can prepared by acylating 6-methoxy-2-tetralone with dimethyl carbonate by the method similar Verba et al. [15], which is incorporated herein by reference in its entirety.

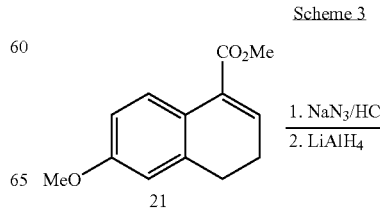

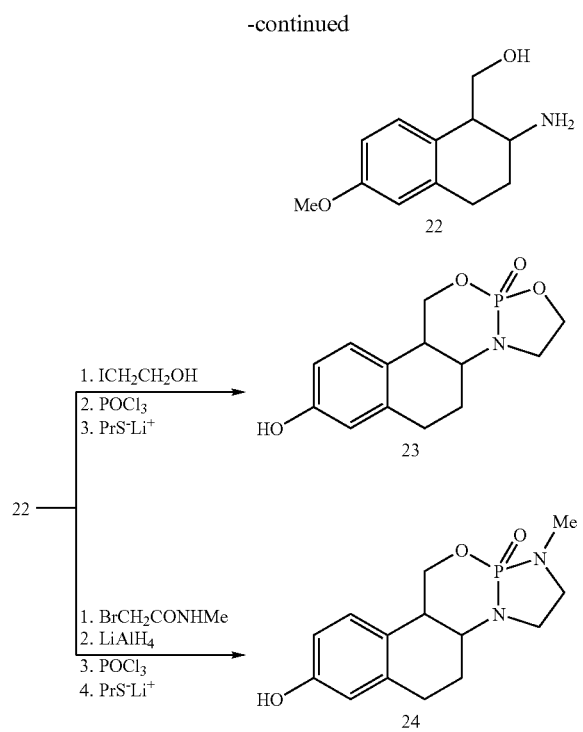

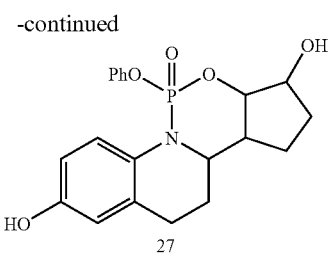

Compounds of the present invention may exist as as a single stereoisomer or as mixture of enantiomers and diastereomers whenever chiral centers are present. Individual stereoisomers can be isolated by the methods well known in the art: diastereomers can be separated by standard purification methods such as fractional crystallization or chromatography, and enantiomers can be separated either by resolution or by chromatography using chiral columns.

The phosphasteroids of the present invention is useful in therapy and diagnostic imaging of respective steroid receptor containing lesions. The present invention is also applicable for the development of compounds with full or partial agonistic, antagonistic, and inverse agonistic properties at the respective steroid receptors at different tissues for diagnostic and therapeutic purposes.

The compounds of the present invention can be administered in the pure form, as a pharmaceutically acceptable salt derived from inorganic or organic acids and bases, or as a pharmaceutically 'prodrug.' The pharmaceutical composition may also contain physiologically tolerable diluents, carriers, adjuvants, and the like. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio. Pharmaceutically acceptable salts are well-known in the art, and are described by Berge et al. [16], incorporated herein by reference. Representative salts include, but are not limited to acetate, adipate, alginate, citrate, aspartate, benzoate, benzenesulfonate, chloride, bromide, bisulfate, butyrate, camphorate, camphor sulfonate, gluconate, glycerophosphate, hemisulfate, heptanoate, hexanoate, fumarate, maleate, succinate, oxalate, citrate, hydrochloride, hydrobromide, hydroiodide, lactate, maleate, nicotinate, 2-hydroxyethansulfonate (isothionate), methane sulfonate, 2-naphthalene sulfonate, oxalate, palmitoate, pectinate, persulfate, 3-phenylpropionate, picrate, pivalate, propionate, tartrate, phosphate, glutamate, bicarbonate, p-toluenesulfonate, undecanoate, lithium, sodium, potassium, calcium, magnesium, aluminum, ammonium, tetramethyl ammonium, tetraethylammonium, trimethylammonium, triethylammonium, diethylammonium, and the like.

Compounds belonging to Formula 12 can be prepared by the according to the method similar to the one for the specific steroid mimic 27 outlined in Scheme 4. The acid chloride 24 can be prepared from 3-hydroxyhydrocinnamic acid. The condensation of 24 and 25 can also be effected via the enamine acylation method.

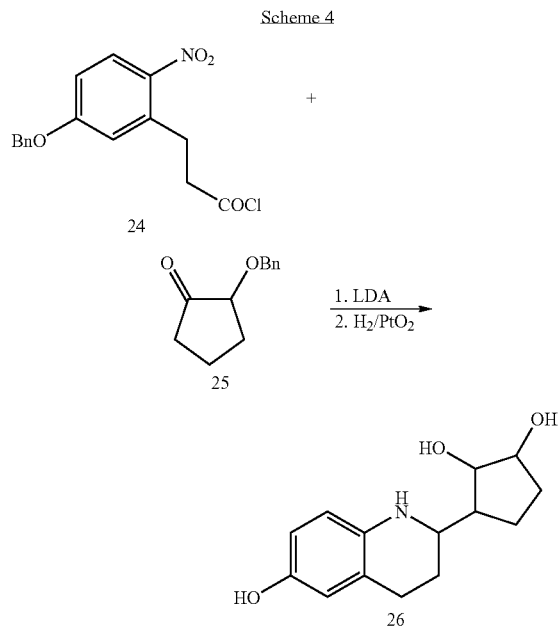

The pharmaceutical compositions of this invention can be administered to humans and other mammals enterally or parenterally in a solid, liquid, or vapor form. Enteral route includes, oral, rectal, topical, buccal, and vaginal administration. Parenteral route intravenous, intramuscular, intraperitoneal, intrasternal, and subcutaneous injection or infusion. The compositions can also be delivered through a catheter for local delivery at a target site, via an intracoronary stent (a tubular device composed of a fine wire mesh), or via a biodegradable polymer. The compositions can also be delivered via an implantable drug delivery devices such as micro miniature mechanical pumps, osmotic pumps, or other similar kind of reservoirs.

The active compound is mixed under sterile conditions with a pharmaceutically acceptable carrier along with any needed preservatives, excipients, buffers, or propellants. Opthalmic formulations, eye ointments, powders and solutions are also contemplated as being within the scope of this invention. Actual dosage levels of the active ingredients in the pharmaceutical formulation can be varied so as to achieve the desired therapeutic response for a particular patient. The selected dosage level will depend upon the activity of the particular compound, the route of administration, the severity of the condition being treated, the sensitivity of the target lesions, and prior medical history of the patient being treated. However, it is within the skill of the art to start doses of the compound at levels lower than required to achieve the desired therapeutic effect and to increase it gradually until optimal therapeutic effect is achieved. The total daily dose of the compounds of this invention administered to a human or lower animal may range from about 0.0001 to about 1000 mg/kg/day. For purposes of oral administration, more preferable doses can be in the range from about 0.001 to about 5 mg/kg/day. If desired, the effective daily dose can be divided into multiple doses for purposes of administration; consequently, single dose compositions may contain such amounts or submultiples thereof to make up the daily dose.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated, the severity of the disorder; sensitivity of the disorder; activity of the specific compound employed; the specific composition employed, age, body weight, general health, sex, diet of the patient; the time of administration, route of administration, and rate of excretion of the specific compound employed, and the duration of the treatment. The compounds of the present invention may also be administered in combination with other drugs if medically necessary.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof. These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Prolonged absorption of the injectable pharmaceutical form can be brought about by the use of agents delaying absorption, for example, aluminum monostearate and gelatin. Proper fluidity can be maintained, for example, by the use of coating materials such as lecithin, by the maintenance of the required particle size in the case of dispersions, and by the use of surfactants. In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Dosage forms for topical administration include powders, sprays, ointments and inhalants. Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The present invention also provides pharmaceutical compositions that comprise compounds of the present invention formulated together with one or more non-toxic pharmaceutically acceptable carriers. Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together. Methods to form liposomes are known in the art [16], incorporated herein by reference.

The compounds of the present invention can also be administered to a patient in the form of pharmaceutically acceptable 'prodrugs.' The term "pharmaceutically acceptable prodrugs" as used herein represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

Prodrugs of the present invention may be rapidly transformed in vivo to the parent compound of the above formula, for example, by hydrolysis in blood. A thorough discussion is provided in the literature [18, 19], incorporated herein by reference.

The Examples presented below describe preferred embodiments and utilities of the invention and are not meant to limit the invention unless otherwise stated in the claims appended hereto. The description is intended as a non-limiting illustration, since many variations will become apparent to those skilled in the art in view thereof. It is intended that all such variation within the scope and spirit of the appended claims be embraced thereby. Changes can be made in the composition, operation, and arrangement of the method of the present invention described herein without departing from the concept and scope of the invention as defined in the claims.

EXAMPLE 1

Preparation of Phosphasteroid Mimic 12

Step 1. A solution of cyanoacetic acid (22 mmol) and tritheylamine (45 mmol) in methylene chloride (20 mL) is stirred and cooled to 0° C. Isobutylchloroformate (22 mmol) is added dropwise to the above mixture at such a rate that the internal temperature is maintained at 0–5° C. and the entire mixture is allowed to stir at this temperature for 1 hour. A solution of 3-methoxyphenylethylamine (20 mmol) in methylene chloride (10 mL) is added in portions and the entire mixture is then allowed to stir at ambient temperature for 4 hours. The reaction mixture is poured onto water and the organic layer is separated, washed with 5% HCl, saturated sodium bicarbonate, and brine. The organic layer is dried over anhydrous magnesium sulfate, filtered, and the filtrate evaporated in vacuo to give the desired cyanoacetamide derivative, which can be used as such for the next step.

Step 2. A solution of the cyanoacetamide (10 mmol) from Step 1 in anhydrous, ethanol-free chloroform (20 mL) is treated with phosphorous oxychloride (12 mmol) and the mixture is stirred and heated under reflux for 16 hours. The reaction mixture is diluted with chloroform (20 mL) and poured onto saturated sodium bicarbonate solution (100 mL). The organic layer is separated, washed with brine, dried over anhydrous magnesium sulfate, filtered, and the filtrate evaporated in vacuo to give the desired dihydroisoquinoline derivative, which is purified by chromatography or recrystallization.

Step 3. A solution of the dihydroisoquinoline from (10 mmol) from Step 2 is dissolved in anhydrous methanol (30 mL), treated with magnesium metal (12 mmol) and stirred and heated under reflux for 16 hours. The reaction mixture is evaporated in vacuo and the residue is treated with water (50 mL), and extracted with methylene chloride (50 mL). The organic layer is separated, washed with brine, dried over anhydrous magnesium sulfate, filtered, and the filtrate evaporated in vacuo to give the desired cyanomethyl tetrahydroisoquinoline derivative, which is purified by chromatography or recrystallization.

Step 4. A solution of the cyano derivative (10 mmol) from Step 3 is dissolved in methylene chloride (20 mL), is treated with di-t-butyldicarbonate (12 mmol) and stirred at ambient temperature for 16 hours. The solvent is evaporated in vacuo, and the crude material is purified by chromatography or recrystallization.

Step 5. A solution of the nitrile derivative (10 mmol) from Step 4 is dissolved in methanol (30 mL), and carefully treated with Adam's catalyst ($PtO_2$) (200 mg) and glacial acetic acid (1 mL). The mixture is hydrogenated at about 50 psi (3.6 atm) for 16 hours. The reaction mixture is filtered through Celite and the filtrate is evaporated in vacuo. The crude material is purified by chromatography or recrystallization.

Step 6. A mixture of the amine (10 mmol) from Step 5, dimethyl 2-ketomalonate (11 mmol), and acetic acid (5 mL) is carefully treated with sodium cyanoborohydride (12 mmol). The entire mixture is stirred at ambient temperature for 16 hours, and thereafter the solvent is evaporated in vacuo. The residue is treated with water (50 mL) and methylene chloride (50 mL). The organic layer is separated, washed with saturated sodium bicarbonate followed by brine, dried over anhydrous magnesium sulfate, filtered, and the filtrate evaporated in vacuo to give the desired diester, which is purified by chromatography or recrystallization.

Step 7. A solution of the diester (10 mmol) from Step 6 in anhydrous tetrahydrofuran (25 mL) is stirred and cooled to 0° C. under inert atmosphere. A solution of lithium aluminum hydride (1M in THF) is added dropwise such that the temperature is maintained at 0–5° C. After the addition, the mixture is heated under reflux for 4 hours after which time the reaction is again cooled to 0° C. Requisite amount of ice-cold water is added dropwise while maintaining the temperature at 0–5° C. Once all the excess lithium aluminum hydride is decomposed, the reaction mixture is diluted with additional THF (30 mL) and treated with anhydrous sodium sulfate and kept at ambient temperature for 30 minutes. The mixture is then filtered, and the filtrate evaporated in vacuo. The residue is dissolved in methylene chloride (20 mL), treated with trifluoroacetic acid (10 mL), and kept at ambient temperature for 2 hours. Thereafter, the solvent and excess TFA is removed by evaporation in vacuo to give the desired aminodiol which is used as such for the next step.

Step 8. A solution of the aminodiol (10 mmol) from Step 7 in anhydrous, ethanol-free chloroform (20 mL) is treated with phosphorous oxychloride (12 mmol) and the mixture is stirred and heated under reflux for 16 hours. The reaction mixture is diluted with chloroform (20 mL) and poured onto saturated sodium bicarbonate solution (100 mL). The organic layer is separated, washed with brine, dried over anhydrous magnesium sulfate, filtered, and the filtrate evaporated in vacuo to give the desired the methyl ether of the steroid mimic, which is purified by chromatography or recrystallization.

Step 9. A mixture of the methyl ether (10 mmol) from Step 8 in anhydrous, dimethylformamide (10 mL) and lithium propylmercaptide (20 mmol) is heated at 80–90° C. for 16 hours. Excess solvent is removed by evaporation in vacuo, and the residue is treated with 5% HCl (10 mL) and water (50 mL) and extracted with methylene chloride (50 mL). The organic layer is separated, washed thoroughly with water, dried over anhydrous sodium sulfate, filtered, and the filtrate evaporated in vacuo to give the desired phosphorous steroid mimic 12, which is purified by chromatography or recrystallization.

EXAMPLE 2

Preparation of Phosphasteroid Mimic 16

Step 1: A mixture of 3-hydroxypyrrolidine-2-acetic acid lactone (10 mmol) and di-t-butyldicarbonate (11 mmol) in methylene chloride (20 mL) is stirred at ambient temperature for 16 hours. The solvent is evaporated in vacuo, and the crude material is purified by chromatography or recrystallization.

Step 2. A mixture of the Boc-protected lactone (10 mmol) from Step 2, 2-amino-5-hydroxybenzylalcohol dimethyl ether (10 mmol), and p-TsOH (0.5 mol) in anhydrous dimethylformamide (10 mL) and lithium propylmercaptide (20 mmol) is heated at 80–90° C. for 16 hours. Excess solvent is removed by evaporation in vacuo, and the residue is treated with 5% HCl (10 mL) and water (50 mL) and extracted with methylene chloride (50 mL). The organic layer is separated, washed thoroughly with water, dried over anhydrous magnesium sulfate, filtered, and the filtrate evaporated in vacuo to give the desired phosphorous steroid mimic, which is purified by chromatography or recrystallization.

Step 3. A solution of the diester (10 mmol) from Step 6 in anhydrous tetrahydrofuran (25 mL) is stirred and cooled to 0° C. under inert atmosphere. A solution of diborane (30 mL) (1M in THF) is added dropwise such that the temperature is maintained at 0–5° C. After the addition, the mixture is heated under reflux for 16 hours after which time the reaction is again cooled to 0° C. Requisite amount of ice-cold water is added dropwise while maintaining the temperature at 0–5° C. Once all the excess diborane is decomposed, the reaction mixture is treated with water (30 mL) and extracted with methylene chloride. The organic layer is separated, washed with brine, dried over anhydrous sodium sulfate, filtered, and the filtrate evaporated in vacuo. The crude product is purified by chromatography or recrystallization.

Step 4: The purified Boc-protected compound from Step 3 is dissolved in methylene chloride (20 mL), treated with trifluoroacetic acid (10 mL), and kept at ambient temperature for 2 hours. Thereafter, the solvent and excess TFA is removed by evaporation in vacuo to give the desired aminodiol which is used as such for the next step.

Step 5. A solution of the dibenzyl ether from Step 4 (10 mmol) from Step 4 is dissolved in methanol (30 mL), and carefully treated with 10% Pd—C (200 mg). The mixture is hydrogenated at about 50 psi (3.6 atm) for 4 hours. The reaction mixture is filtered through Celite and the filtrate is evaporated in vacuo. The residue is treated with saturated sodium bicarbonate (20 mL) and methylene chloride (30 mL). The organic layer is separated, washed thoroughly with water, dried over anhydrous sodium sulfate, filtered, and the filtrate evaporated in vacuo. The residue used as such for the next step.

Step 6. A solution of the aminodiol (10 mmol) from Step 5 in anhydrous, ethanol-free chloroform (20 mL) is treated with phosphorous oxychloride (12 mmol) and the mixture is stirred and heated under reflux for 16 hours. The reaction mixture is diluted with chloroform (20 mL) and poured onto saturated sodium bicarbonate solution (100 mL). The organic layer is separated, washed with brine, dried over anhydrous magnesium sulfate, filtered, and the filtrate evaporated in vacuo to give the desired steroid mimic 16, which is purified by chromatography or recrystallization.

EXAMPLE 3

Preparation of Iphosphasteroid Mimic 19

Step 1: The procedure is identical to Step 1 in Example 1, except that malonic acid monomethyl ester is used instead of cyanoacetic acid; all other reagents and solvents are the same. The crude unsaturated ester is purified by chromatography or recrystallization.

Step 2: A mixture of the unsaturated ester from Step 1 (10 mmol) and sodium azide (30 mmol) in methanol is treated with trifluoroacetic acid (30 mmol) and allowed to stir at ambient temperature for 16 hours. If the reaction is not completed by this time additional quantities of sodium azide and trifluoroacetic acid may be added. The reaction mixture is poured onto saturated sodium bicarbonate and extracted with methylene chloride. The organic layer is separated, washed with brine, dried over anhydrous magnesium sulfate, filtered, and the filtrate evaporated in vacuo to give the desired azide, which is purified by chromatography or recrystallization.

Step 3. A solution of the azidoester (10 mmol) from Step 2 in anhydrous tetrahydrofuran (25 mL) is stirred and cooled to 0° C. under inert atmosphere. A solution of lithium aluminum hydride (1M in THF) is added dropwise such that the temperature is maintained at 0–5° C. After the addition, the mixture is heated under reflux for 4 hours after which time the reaction is again cooled to 0° C. The workup of the reaction is carried out exactly as described in Step 7, Example 1. The crude material is used as such for the next step.

Step 4. A mixture of the amine from Step 3 (10 mmol), 2-iodoethanol (12 mmol), and finely-ground anhydrous potassium carbonate (20 mmol) in glyme (20 mL) is heated under reflux for 6 hours. The reaction mixture is then cooled and filtered. The filtrate is evaporated in vacuo to give the desired aminodiol, which is purified by chromatography or recrystallization.

Step 5. The aminodiol from Step 4 is phosphorylated by the same procedure described in Step 8, Example 1 to give the desired methylether of the steroid mimic, which is purified by chromatography or recrystallization.

Step 6: The final conversion of the methyl ether to the desired steroid mimic 19 is accomplished in the same manner as described in Step 9, Example 1.

EXAMPLE 4

Preparation of Phosphasteroid Mimic 24

Step 1: A solution of diisopropylamine (15 mmol) in anhydrous THF is stirred and cooled to −30° C. in an inert atmosphere. Thereafter n-BuLi (17 mmol) (2 M solution in hexane) is then added via a syringe. The solution is stirred at about −30° C. for 30 minutes and treated with 2-benzyloxycyclopentanone (11 mmol). The entire mixture is stirred at this temperature for 30 minutes and treated with 5-benzyloxy-2-nitrophenylacetyl chloride (10 mmol). The mixture is allowed to reach ambient temperature and stirred at this temperature for 4 hours. The reaction mixture is poured onto water and extracted with methylene chloride. The organic layer is separated, washed with brine, dried over anhydrous magnesium sulfate, filtered, and the filtrate evaporated in vacuo to give the desired nitro compound, which is purified by chromatography or recrystallization.

Step 2. A solution of the nitro derivative (10 mmol) from Step 1 is dissolved in methanol (30 mL), and carefully treated with Adam's catalyst (PtO$_2$) (200 mg) and glacial acetic acid (1 mL). The mixture is hydrogenated at about 50 psi (3.6 atm) for 16 hours. The reaction mixture is filtered through Celite and the filtrate is evaporated in vacuo. The crude amino diol is purified by chromatography or recrystallization.

Step 3. A solution of the aminodiol (10 mmol) from Step 2 in anhydrous, ethanol-free chloroform (20 mL) is treated with phenylphosphodichloridate (12 mmol) and the mixture is stirred and heated under reflux for 16 hours. The reaction mixture is diluted with chloroform (20 mL) and poured onto saturated sodium bicarbonate solution (100 mL). The organic layer is separated, washed with brine, dried over anhydrous magnesium sulfate, filtered, and the filtrate evaporated in vacuo to give the desired the steroid mimic 24, which is purified by chromatography or recrystallization.

REFERENCES

1. Wagner, H. N.; Szabo, M. D.; Buchanan, J. W. (Eds.). *Principles of Nuclear Medicine*. Saunders: Philadelphia, 1995.
2. Chi, D. Y.; O'Neil, J. P.; Anderson, C. J.; Welsh, M. J.; Katzenellenbogen, J. A. Homodimeric and heterodimeric bis(amino thiol) oxometal complexes with rhenium(V) and technetium(V). Control of heterodimeric complex formation and an approach to metal complexes that mimic steroid hormones. *J. Med. Chem.* 1994, 37, 928–937.
3. Rajagopalan, R. Nitrogen sulfur ligands as opiate receptor drug mimics. U.S. Patent 1994: U.S. Pat. No. 5,330,737.
4. Rajagopalan, R. Metal containing steroid mimics and ligands useful in the preparation thereof. U.S. Patent 1997: U.S. Pat. No. 5,602,236.
5. Chi, D. Y.; Katzenellenbogen, J. A. Selective formation of heterodimeric aminothiol oxometal complexes of rhenium(V). *J. Am. Chem. Soc.* 1993, 115, 7045–7046.
6. Hom, R. K.; Katzenellenbogen, J. A. Synthesis of oxorhenium(V) complex mimic of a steroidal estrogen. *J. Org. Chem.* 1997, 62, 6290–6297.
7. Skaddan, M. B.; Katzenellenbogen, J. A. Integrated oxorhenium(V) complexes as estrogen mimics. *Bioconjugate. Chem.* 1999, 10, 119–129.
8. Bodlaski, R., et al. An efficient synthesis of the entantiomeric 17-phosphasteroid system. *J. Org. Chem.* 1982, 47(11), 2219–2220.
9. Symmes, C.; Morris, J.; Quin, L. D. A new synthesis of phosphasteroids employing the McCormack cycloaddition for construction of the D-ring. *Tetrahedron Letters* 1977, 4, 335–338.
10. Miller, W. R. In *Estrogen and Breast Cancer*, Medical Intelligence Unit; R. G. Landes Co. and Chapman and Hall: New York, 1996.
11. Skaddan, M. B.; Wust, F. R.; Katzenellenbogen, J. A. Synthesis and binding affinities of novel Re-containing 7α-substituted estradiol complexes: Models for breast cancer imaging agents. *J. Org. Chem.* 1999, 64, 8108–8121.
12. DiZio, J. P.; Anderson, C. J.; Davidson, A.; Ehrhardt, G. I.; Carlson, K. E.; Welsh, M. J.; Katzenellenbogen, J. A. Technetium- and rhenium-labeled progestins: Synthesis, receptor binding, and in vivo distribution of an 11β-substituted progestin labeled with technetium-99 and rhenium-186. *J. Nucl. Med.* 1992, 33, 558–569.
13. El Amouri, H.; Vessieres, A.; Vichard, D.; Top, S.; Gruselle, M.; Jaouen, G. Syntheses and affinities of novel organanometallic-labeled estradiol derivatives: A structure-activity relationship. *J. Med. Chem.* 1992, 35, 3130–3135.
14. Geissman, T. A.; Waiss, A. C. Total synthesis of (±)retronecine. *J. Am. Chem. Soc.* 1993, 115, 7045–7046.
15. Verba, J; Carrie, R. *Tetrahedron* 1983, 39(24), 4163–4174.
16. S. M. Berge et al. *J. Pharmaceutical Sciences* 1977, 66, 1 et seq.
17. T. Higuchi and V. Stella. Pro-drugs as Novel Delivery Systems, V. 14. A.C.S. Symposium Series, 1987.
18. Edward B. Roche (Ed.). *Bioreversible Carriers in Drug Design*. American Pharmaceutical Association and Pergamon Press: New York 1987.

19. Prescott, Ed., *Methods in Cell Biology*, Volume XIV, pp. 33 et seq. Academic Press, New York, 1976.

What is claimed is:

1. A compound of Formula 9,

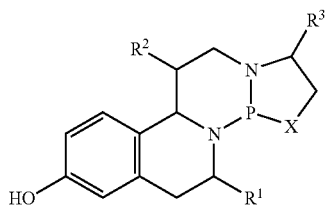

Formula 9 wherein P is —P— or —P═O; X is —O— or —NR$^4$; R$^1$ to R$^3$ are independently selected from the group consisting of hydrogen; $C_1$–$C_{10}$ alkyl; carboxyl; $C_1$–$C_{10}$ hydroxyalkyl; $C_1$–$C_{10}$ alkoxycarbonyl; $C_5$–$C_{10}$ aryl unsubstituted or substituted with $C_1$–$C_{10}$ alkyl, hydroxyl, $C_1$–$C_{10}$ alkoxyl, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and R$^4$ is selected from the group consisting of hydrogen; $C_1$–$C_{10}$ alkyl; $C_1$–$C_{10}$ acyl; $C_1$–$C_{10}$ hydroxyalkyl; $C_5$–$C_{10}$ aryl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl; and $C_5$–$C_{10}$ arylalkyl unsubstituted or substituted with $C_1$–$C_{10}$ alkyl, hydroxyl, $C_1$–$C_{10}$ alkoxyl, cyano, halo, trihaloalkyl, carboxyl, $C_1$–$C_{10}$ acyl, $C_1$–$C_{10}$ hydroxyalkyl, amino, $C_1$–$C_{10}$ alkylamino, $C_1$–$C_{10}$ dialkylamino, and $C_1$–$C_{10}$ alkoxycarbonyl.

2. The compound of claim 1, wherein P is —P═O; X is —O— or —NR$^4$; R$^1$ to R$^3$ are independently selected from the group consisting of hydrogen; $C_1$–$C_{10}$ alkyl; $C_5$–$C_{10}$ aryl unsubstituted or substituted with $C_1$–$C_{10}$ alkyl, hydroxyl, $C_1$–$C_{10}$ alkoxyl, trihaloalkyl, and halo; $C_5$–$C_{10}$ arylalkyl unsubstituted or substituted with $C_1$–$C_{10}$ alkyl, hydroxyl, $C_1$–$C_{10}$ alkoxyl, trihaloalkyl, and halo; and R$^4$ is selected from the group consisting of hydrogen; $C_1$–$C_{10}$ alkyl; $C_1$–$C_{10}$ hydroxyalkyl; $C_1$–$C_{10}$ acyl, and $C_1$–$C_{10}$ alkoxycarbonyl.

3. The compound of claim 1, wherein P is —P═O; X is —O— or —NR$^4$; R$^1$ to R$^3$ are hydrogen; and R$^4$ is hydrogen, $C_1$–$C_{10}$ alkyl, $C_1$–$C_{10}$ acyl, or $C_1$–$C_{10}$ alkoxycarbonyl.

4. The compound of claim 1, wherein P is a radioactive isotope of phosphorous.

* * * * *